United States Patent
Smith

(10) Patent No.: US 12,006,284 B2
(45) Date of Patent: Jun. 11, 2024

(54) UPGRADING OF FUSEL OILS OVER DOPED ALUMINA

(71) Applicant: Gevo, Inc., Englewood, CO (US)

(72) Inventor: Jonathan Smith, Highlands Ranch, CO (US)

(73) Assignee: Gevo, Inc., Englewood, CO (US)

( * ) Notice: Subject to any disclaimer, the term of this patent is extended or adjusted under 35 U.S.C. 154(b) by 0 days.

(21) Appl. No.: 17/675,840

(22) Filed: Feb. 18, 2022

(65) Prior Publication Data

US 2022/0234969 A1 Jul. 28, 2022

Related U.S. Application Data

(63) Continuation of application No. PCT/US2020/046931, filed on Aug. 19, 2020.

(60) Provisional application No. 62/889,787, filed on Aug. 21, 2019.

(51) Int. Cl.
*C07C 5/22* (2006.01)
*C07C 1/24* (2006.01)

(52) U.S. Cl.
CPC .............. *C07C 5/2213* (2013.01); *C07C 1/24* (2013.01)

(58) Field of Classification Search
None
See application file for complete search history.

(56) References Cited

U.S. PATENT DOCUMENTS

| 5,227,563 A * | 7/1993 | Fukuhara ................. B01J 21/04 585/639 |
| 10,633,320 B2 | 4/2020 | Smith |
| 2013/0108530 A1 | 5/2013 | Chang et al. |
| 2013/0204058 A1 * | 8/2013 | Adam ................... C12P 5/026 585/329 |
| 2017/0226028 A1 | 8/2017 | Smith et al. |
| 2021/0040012 A1 * | 2/2021 | Richardson ............... C07C 2/08 |

FOREIGN PATENT DOCUMENTS

| WO | 2019136283 A1 | 7/2019 |
| WO | 2021034898 A1 | 2/2021 |

OTHER PUBLICATIONS

International Search Report and Written Opinion received for PCT Application No. PCT/US2020/046931, dated Nov. 10, 2020, 10 pages.
Extended European Search Report for Application No. EP 20854053.4, dated Aug. 21, 2023, 8 pages.
Chiesa et al. (1990) "Selective Formation of 2-methyl-2-butene and 2-methyl-1-butene: Operating Conditions and Kinetic Analysis", Canadian Journal of Chemical Engineering, 68(5):807-813.
Murray et al. (1946) "The Catalytic Hydration of the Amyl Alcohols of Fusel Oil With a Kaolin Catalyst of High Activity", Journal of the Council for Scientific and Industrial Research, 19:438-441.

* cited by examiner

*Primary Examiner* — In Suk C Bullock
*Assistant Examiner* — Alyssa L Cepluch
(74) *Attorney, Agent, or Firm* — Mintz, Levin, Cohn, Ferris, Glovsky and Popeo, P.C.

(57) ABSTRACT

This present disclosure relates to a catalytic process for upgrading crude and/or refined fusel oil mixtures to higher value renewable 2-methyl-2-butene, via novel doped alumina catalysts. It was found that passing a vaporized stream of crude and/or refined fusel oils over doped alumina catalysts provides renewable 2-methyl-2-butene in high yields in a single step. Subsequent downstream purification of the reactor effluent results in a renewable 2-methyl-2-butene at competitive price and quality to fossil fuel derived 2-methyl-2-butene.

18 Claims, No Drawings

UPGRADING OF FUSEL OILS OVER DOPED ALUMINA

CROSS-REFERENCES TO RELATED APPLICATIONS

This application is a continuation application, filed under 35 U.S.C. § 120, of PCT International Paten Application No. PCT/US2020/046931 with an International Filing Date of Aug. 19, 2020, and entitled "Upgrading of Fusel Oils Over Doped Alumina," which claims the benefit of U.S. Provisional Patent Application No. 62/889,787 filed on Aug. 21, 2019, and entitled "Upgrading of Fusel Oils Over Doped Alumina," the disclosure of all of which are incorporated herein by reference in their entireties.

TECHNICAL FIELD

The subject matter described herein relates to a process for converting fusel oils comprising $C_2$-$C_6$ alcohols to renewable chemicals. The renewable chemicals comprise bio-based olefins which are useful as precursors for iso-octane, gasoline, jet fuel, or diesel fuel production.

BACKGROUND OF THE INVENTION

Fusel oils are formed as a by-product of alcoholic fermentation, and consist of a mixture of several alcohols comprised mainly of amyl alcohols along with lesser amounts of ethanol, propanol, n-butanol, and isobutanol. In many cases, these so-called fusel oils are re-added back into the ethanol product at some level, burned as fuel, or further purified and sold on the open market.

Depending on the sugar source for the fermentation process, and the organism used, fusel oil levels are typically between 0.2-3.0% as a relative percent of the target alcohol produced. Metabolites involved in fermentation processes have been identified as a source of the production of these higher alcohols. Also amine nitrogen assimilation may play a role in the production of fusel oils. Considering the high content of amyl alcohols in fusel oil, it is important to mention the role played by leucine and isoleucine as source molecules of 3-methyl-1-butanol and 2-methyl-1-butanol, respectively, which indicates that fusel oil is formed from α-keto acids, derived from amino acids. The exact composition of the fusel oil may vary based on the feedstock used for the fermentation. Results indicate that butanol and i-amyl alcohols content increases when molasses and fruits are the raw material for fermentation. However, it should be noted that pH in the fermenter may significantly affect the composition and production of the higher alcohols.

Raw fusel oil is usually a relatively viscous liquid with a dark-reddish color, and a very unpleasant odor. As a result of these properties, the direct utilization of fusel oil as a solvent has been very limited. In some countries it is burned to supply energy for the ethanol processing plants. In some places, it is used mainly for denaturation of alcohol, or for removing the foam from molasses during sugar manufacturing. A substantial portion of it, however, has historically been discarded.

Due to its potential as feedstock for the synthesis of heavier oxygenates, interest in conversion of these higher alcohols is growing. For example, U.S. Pat. No. 10,633,320 discloses passing a vaporized stream of crude and/or refined fusel oils over mixed metal oxide catalysts, metal doped zeolites, or non-metal doped zeolites and/or metal oxides. Catalysts and processes according to the this patent tend to produce of higher levels of 2-methyl-1,3-butadiene and 3-methyl-1-butene, which may be less the desirable than 2-methyl-2-butene depending on the end application.

BRIEF SUMMARY OF THE INVENTION

Aspects of the current subject matter relate inter alia to processes for converting fusel oils comprising $C_2$-$C_6$ alcohols into bio-based olefins.

Consistent with some aspects of the current subject matter, a process for converting fusel oils containing one or more $C_2$-$C_6$ linear or branched alcohols into renewable chemicals is disclosed. The process includes contacting a feed stream comprising the fusel oils with an alumina catalyst comprising one or more of Zr, Ti, Si, or F in a neutral or an ionic form, at a temperature of from 200° C. to 500° C., and a WHSV of at least 1.0, and forming the renewable chemical. The renewable chemical comprises 2-methyl-2-butene in at least 50% yield.

In variations, one or more of the following features may be included in any feasible combination. For example, the one or more $C_{2-6}$ linear or branched alcohols can be one or more $C_2$-$C_5$ alcohols. The fusel oils may be crude or refined fusel oils and further comprise water in an amount of 10 wt. % to 20 wt. % including all subranges therebetween. The renewable chemicals can be formed by dehydrating and isomerizing the $C_2$-$C_6$ linear or branched alcohols into corresponding $C_2$-$C_6$ olefins. The yield of the renewable chemicals such as 2-methyl-2-butene can be at least 50% yield.

Consistent with some aspects of the current subject matter, the alumina catalyst comprises one or more of Zr, Ti, Si, or F in ionic form. The alumina catalyst can comprise ionic Zr and be regenerated via air at a temperature of 400° C. to 600° C., including all subranges therebetween. The alumina catalyst can be regenerated in 30 minutes to 3 hours, including all subranges therebetween.

The process operates at a reaction temperature of 250 to 450° C., and a reaction pressure of 0 psig to 100 psig, including all subranges therebetween. The WHSV for the process can be at least 1. For example, the process includes contacting a feed stream comprising the fusel oils with an γ-alumina catalyst comprising one or more of Zirconium (IV), at a temperature of 420° C., and a WHSV of at least 1.0, and forming the renewable chemical comprises 2-methyl-2-butene in about 60% yield.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

DETAILED DESCRIPTION

Aspects of the current subject matter overcome the challenges described above by providing processes in which doped alumina catalysts are used in fusel oil upgrading reactions to produce industrially relevant olefins in high yield and selectivity at competitive costs. Crude fusel oil mixtures are characterized by higher levels of residual $C_2$-$C_4$ alcohols and water. This is a result of mixture not being subjected to rigorous separation of the fusel oil including $C_5$ alcohols such as 3-methyl-1-butanol and 2-methyl-1-butanol. Whereas, refined fusel oil mixtures have been subjected to separation processes that result in higher concentrations of fusel oil, including $C_5$ alcohols, relative to $C_2$-$C_4$ alcohols, and normally lesser amounts of water. In either case, the catalysts described herein provide options to valorize both types of fusel oil mixtures to higher value renewable chemicals desired by the chemical industry. Renewable chemicals of interest formed via these upgrading platforms are comprised of, but not limited to, methyl isobutyl ketone (MIBK), di-isobutyl ketone (DIBK), 2-methyl-2-butene, 2-methyl-1-butene, isoprene, aldehydes, esters, and other asymmetric ketones.

Low cost bio-based fusel oil mixtures can be converted in high yield to desirable, bio-based $C_4$-$C_5$ olefins. The distribution and selectivity of the olefinic product mixes can be controlled by adjusting catalyst composition, reaction temperature, feed composition, and/or flow rates. The use of γ-alumina for fusel oil dehydration results in a mixture of 3-methyl-1-butene, 1-methyl-2-butene, and 2-methyl-2-butene. Upon in-situ isomerization, the mixture of olefins results in higher yields of cost competitive, bio-based 2-methyl-2-butene. Surprisingly, it was found that utilizing a zirconated γ-alumina, as well as silicated, titanated, or fluorinated γ-alumina results in higher levels of in-situ isomerization of 3-methyl-1-butene to 1-methyl-2-butene and 2-methyl-2-butene isomers (i.e. isoamylene) without concomitant formation of unwanted close boiling linear $C_5$ olefins, which reduce the quality of isolated 2-methyl-2-butene, resulting in improved yields. The level of 3-methyl-1-butene can be further minimized by increasing reaction temperature, but this results in an increase in byproducts thereby reducing the 2-methyl-2-butene purity. Subsequent distillation of the crude product mixes provides access to cost competitive industrially relevant renewable 2-methyl-2-butene.

In the following description, certain specific details are set forth in order to provide a thorough understanding of various embodiments. However, one skilled in the art will understand that the disclosure may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed disclosure.

Reference throughout this specification to "one embodiment" or "an embodiment" means a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The word "about" when immediately preceding a numerical value means a range of plus or minus 10% of that value, e.g., "about 50" means 45 to 55, "about 25,000" means 22,500 to 27,500, etc. Furthermore, the phrases "less than about" a value or "greater than about" a value should be understood in view of the definition of the term "about" provided herein.

"Crude fusel oil" refers to fusel oils produced as a by-product of alcohol fermentation which has not been distilled or treated to obtain a more concentrated $C_5$ alcohol level.

"Refined fusel oil" refers to fusel oils that are distilled or treated to remove the light $C_2$-$C_4$ alcohols and/or water resulting in a more concentrated $C_5$ alcohol level which is then distilled or treated a second time to remove the $C_5$ alcohols from the heavy boiling components.

Disclosed herein is a process for converting fusel oils containing one or more $C_2$-$C_6$ linear or branched alcohols to renewable chemicals, the process includes contacting a feed stream comprising the fusel oils with an alumina catalyst at a temperature of from 200° C. to 500° C., and a WHSV of at least 1.0, wherein the alumina catalyst comprises one or more of Zr, Ti, Si, or F in neutral or ionic form; and forming the renewable chemicals, wherein the renewable chemicals comprise of 2-methyl-2-butene in at least 50% yield.

The reaction can be performed in a continuous mode for mass production of bio-based olefins. The continuous mode can be operated in a fixed bed reactor, and the reactant flows can be upward or downward. The reaction can optionally be performed a batch mode or a semi-continuous mode in suitable reactors.

The $C_2$-$C_6$ linear or branched alcohols useful in the present disclosure includes any $C_2$-$C_6$ linear or branched alcohol known by one of skill in the art. For example the $C_2$-$C_6$ alcohols can be one or more of ethanol, propanol, iso-propanol, 1-butanol, isobutanol, 2-butanol, tert-butanol, pentanol, 3-methyl-1-butanol, 2-methyl-1-butanol, 2,2-dimethyl-1-propanol, 3-pentanol, 2-pentanol, 3-methyl-2-butanol, 2-methyl-2-butanol, hexanol, 2-hexanol, 3-hexanol, 2-methyl-1-pentanol, 3-methyl-1-pentanol, 4-methyl-1-pentanol or other $C_6$ alcohol isomers.

Consistent with some aspects of the subject matter, the one or more $C_2$-$C_6$ linear or branched alcohols is ethanol, propanol, isopropanol, 1-butanol, isobutanol, 2-butanol, tert-butanol, pentanol, 3-methyl-1-butanol, 2-methyl-1-butanol, 2,2-dimethyl-1-propanol, 3-pentanol, 2-pentanol, 3-methyl-2-butanol, 2-methyl-2-butanol, or a combination thereof. Consistent with some aspects of the subject matter, the one or more $C_2$-$C_6$ linear or branched alcohols is ethanol, isobutanol, 3-methyl-1-butanol, 2-methyl-1-butanol or a combination thereof.

Consistent with some aspects of the subject matter, the fusel oil mixture can include water. Water can be present in an amount of about 10 wt. % to 20 wt. %, about 10 wt % to 15 wt. %. or about 12 wt. %. Water can be present, but present in an amount of less than 10 wt. %. Water can present in an amount of about 10 wt. % to 15 wt. %. Water can be present in an amount of about 12 wt. %.

Consistent with some aspects of the subject matter, the fusel oils can include a mixture crude and refined fusel oils. Consistent with some aspects of the subject matter, the fusel oils include crude fusel oils. Consistent with some aspects of the subject matter, the fusel oils include refined fusel oils.

Fusel oil mixtures can comprise one or more of $C_2$-$C_6$ alcohols and water. For example, the fusel oils can include ethanol, isobutanol, 3-methyl-1-butanol, 2-methyl-1-butanol, and water. The 3-methyl-1-butanol may be present in the fusel oils in an amount of 40 wt. % to 70 wt. %. The 3-methyl-1-butanol may be present in 50 wt. % to 70 wt. %. The 3-methyl-1-butanol may be present in the amount of about 54.5 wt. %. The ethanol may be present in an amount of about 1 wt. % to 15 wt. %. The ethanol may be present in an amount of about 6 wt. %. Isobutanol may be present in an amount of 2 wt. % to 25 wt. %. Isobutanol may be present in an amount of 2 wt. % to 8 wt. %. Isobutanol may be present in an amount of 5 wt. % to 6 wt. %.

Further, fusel oils used in the process described herein can comprise a recycled feed stream and/or bio-based alcohols provided from fermentative processes. The renewable chemicals described herein can be useful as precursors for producing gasoline, iso-octane, jet fuel, diesel fuel, or other fuel productions. Renewable chemicals can comprise a mixture of different olefins as known by one of skill in the art. The predominant isomerized renewable $C_5$ olefins, 2-methyl-2-butene and 2-methyl-1-butene, are industrially relevant as they provide access to a renewable raw material that may serve as a direct replacement for $C_5$ olefins typically produced within petroleum refineries.

2-Methyl-2-butene and 2-Methyl-1-butene are usually produced by the deep catalytic cracking (DCC) of vacuum gas oil. DCC is similar to fluid catalytic cracking (FCC) and produces a higher yield of propylene, isobutylene, and 2-methyl-2-butene. With increased demand for propylene, DCC has grown in favor. However, DCC of petroleum-based fossil fuels can be bad for the environment and release harmful emissions. Also, petroleum-based fossil fuels are a finite resource that are not renewable like bio-based resource.

2-Methyl-2-butene is commonly used as a starting material for other products as opposed to being used as is for some final application. These include (i) hydrocarbon resin modification (softening point/Tg/molecular weight control), (ii) fuel additives via oligomerization (typically dimerization) for octane boosters or via etherification with methanol or ethanol, (iii) synthetic building block such as precursor to di-olefins, flavor/fragrance enhancers, antioxidants, typically alkyl phenols, or as synthon for fine chemicals or for pharmaceutical ingredients preparation.

Consistent with some aspects of the subject matter, forming the renewable chemicals comprises dehydrating and isomerizing the $C_2$-$C_6$ linear or branched alcohols into one or more corresponding $C_2$-$C_6$ olefins. In many instances, the renewable chemicals formed are one or more $C_2$-$C_5$ olefins. Specifically, forming the renewable chemicals comprises dehydrating and isomerizing $C_5$ linear or branched alcohols into $C_5$ olefins. The renewable chemicals can also include one or more of butenes, 3-methyl-1-butene, 2-methyl-1-butene, 2-methyl-2-butene, $C_5$ olefins, and $C_2$-$C_3$ olefins.

Fusel oil mixture (i.e. $C_2$-$C_6$ alcohol) single pass conversion in the 2-methyl-2-butene and 2-methyl-1-butene formation reaction is typically higher than about 90%. 3-methyl-1-butene, 2-methyl-1-butene, and 2-methyl-2-butene can comprise at least 80% wt. yield of the renewable chemicals. For example, 3-methyl-1-butene, 2-methyl-1-butene, and 2-methyl-2-butene can comprise at least 90% wt. yield of the renewable chemicals.

Consistent with some aspects of the present subject matter, 2-methyl-2-butene is present in an amount of at least 55 wt. % yield. In some examples, 2-methyl-2-butene is present in an amount of at least 60 wt. % yield. Consistent with some aspects of the present subject matter, 2-methyl-1-butene is present in an amount of at least 15 wt. % yield. In some examples, 2-methyl-1-butene is present in an amount of at least 25 wt. % yield.

The mixtures of bio-based olefins of the present process can be produced in various ratios. For example, 2-methyl-2-butene is formed in a higher ratio than either 2-methyl-1-butene, and 3-methyl-1-butene. Consistent with some aspects of the subject matter, the ratio of 2-methyl-2-butene to 2-methyl-1-butene by wt. % is between 2:1 to 5:1. The ratio of 2-methyl-2-butene to 2-methyl-1-butene by wt. % can also be about 3:1 or 4:1. The ratio of 2-methyl-2-butene to 2-methyl-1-butene by wt. % can be about 2:1. The ratio of 2-methyl-2-butene to 3-methyl-1-butene by wt. % is 10:1 to 20:1 in some embodiments. The ratio of 2-methyl-2-butene to 3-methyl-1-butene by wt. % can be 10:1 to 15:1. More specifically, the ratio of 2-methyl-2-butene to 3-methyl-1-butene by wt. % can be about 13:1. The ratio of 2-methyl-2-butene to 3-methyl-1-butene by wt. % could also be about 10:1. In some embodiments, the ratio of 2-methyl-1-butene to 3-methyl-1-butene by wt. % is between 5:1 to 15:1. The ratio of 2-methyl-1-butene to 3-methyl-1-butene by wt. % can be between 5:1 to 10:1. Consistent with some aspects of the subject matter, the ratio of 2-methyl-1-butene to 3-methyl-1-butene by wt. % is about 5:1.

Granular or extruded catalysts are suitable for the reactions described herein even though no specific size and morphology are mandatory. Catalyst with a size greater than 0.1 mm is more suitable, and the size of 0.2-1.0 mm is most suitable for the operation stability and low pressure drop.

The alumina catalyst comprising Zr, Ti, Si, and/or F (i.e. a doped alumina catalyst) disclosed herein are more stable in the present process as compared to standard commercial grade alumina catalysts. Further, the doped alumina catalyst results in lower yield of 3-methyl-1-butene and higher yields to 2-methyl-2-butene compared to standard alumina catalyst such as γ-alumina. Standard commercial grade alumina catalysts results in formation of 3-methyl-1-butene in yields of 10-15%, which is not ideal. The doped alumina catalyst described herein results in significantly lower yields of 3-methyl-1-butene of about 5% or less than 5%. One significant advantage of doped alumina catalyst of the present disclosure is the production of 2-methyl-2-butene in at least 50% yield, while minimizing the yield of 3-methyl-1-butene to less than 5% yield.

Consistent with some aspects of the subject matter, the alumina catalyst is γ-alumina comprising one or more of Zr (zirconium), Ti (titanium), Si (silicon), or F (fluorine). In some embodiments, the alumina catalyst comprises the Zr. The Zr can be Zirconium (IV). One or more of Zr, Ti, Si, or F can be in an ionic form.

The alumina catalyst includes the one or more of Zr, Ti, Si, or F is present in an amount of about 3 wt. % to 15 wt. %. In some examples, the alumina catalyst includes one or more of Zr, Ti, Si, or F is present in an amount of about 3 wt. % to 10 wt. %. For example, the alumina catalyst includes one or more of Zr, Ti, Si, or F in an amount of about 5 wt. % to 8 wt. %. Unless noted, all catalysts were prepared via the incipient wetness impregnation technique.

The doped alumina catalysts (such as zirconated γ-alumina, silicated, titanated, or fluorinated γ-alumina) utilized for dehydration/isomerization of fusel oils may be regenerated in-situ, via air, as necessary to return catalyst to its' initial activity.

The alumina catalyst can be regenerated as necessary under suitable conditions for the processes described herein. Consistent with some aspects of the subject matter, the alumina catalyst is regenerated in-situ in air. The alumina catalyst can be regenerated at a temperature of 400° C. to 600° C. For example, the alumina catalyst can be regenerated at 500° C. Consistent with some aspects of the subject matter, the alumina catalyst is regenerated for 30 minutes to 3 hours. For example, the alumina catalyst is regenerated for 1 to 2 hours.

The reaction temperature for converting $C_2$-$C_8$ linear or branched olefins to $C_8$-$C_{24}$ hydrocarbons can be any reaction temperature known by one of skill in the art. The temperature used for the reactions according to the present process have unexpectedly resulted in high yield and selectivity of olefins such as 2-methyl-2-butene.

The temperature range can be any useful range known by one of skill in the art. Consistent with some aspects of the reaction, the temperature is from 100° C. to 600° C. Consistent with some aspects of the reaction, the temperature is from 200° C. to 500° C. The temperature can be from 250° C. to 450° C. The temperature can be from 400° C. to 450° C. For example, the temperature can be about 420° C.

Tuning the weight hourly space velocity (WHSV) can be useful for the yield and selectivity of the renewable chemicals. Consistent with some aspects of the subject matter, the WHSV is at least 1. The WHSV can be at least 1.5. The WHSV can be at least 2. For example, the WHSV can be at least 2.5.

The reaction pressure for converting $C_2$-$C_8$ linear or branched alcohols to renewable chemicals comprising 2-methyl-2-butene can be any reaction pressure known by one of skill in the art. Relatively low reaction pressure has surprisingly resulted in high yields and selectivity of 2-methyl-2-butene. For example, the contacting the feed stream comprising fusel oils can be performed at a pressure of 0 psig to 200 psig, 0 psig to 100 psig, 1 psig to 200 psig, or 1 psig to 100 psig.

Consistent with some aspects of the subject matter, contacting the feed stream comprising the fusel oils is performed at a pressure of 0 psig to 100 psig. In some embodiments, the pressure is 1 psig to 100 psig.

The process of converting fusel oils to renewable chemicals comprises a reaction temperature for dehydrating and isomerizing fusel oil mixtures consisting of branched and/or linear $C_2$-$C_5$ alcohols is from 250° C. to 450° C., with reaction pressures ranging from 0-100 psig.

The present disclosure also provides a process for converting one or more $C_2$-$C_6$ linear or branched alcohols contained in fusel oils to renewable chemicals, the process includes contacting a feed stream comprising fusel oils with an alumina catalyst at a temperature of 420° C., and a WHSV of 2.5, wherein the alumina catalyst is γ-alumina and comprises Zirconium (IV); and forming the renewable chemicals, wherein the renewable chemicals are $C_2$-$C_5$ olefins and further comprises 2-methyl-2-butene in about 60% yield.

EXAMPLES

Reactor Set-Up

Fusel oil dehydration to predominantly 2-methyl-2-butene upgrading was carried out at 300° C. to 500° C., via a fixed bed reactor, containing 2.9 g, 5.0 g, or 15 g of specified catalyst, and flowing preheated (160° C.) vaporized fusel oils in a downward flow over the fixed catalyst bed while in some cases co-feeding nitrogen at atmospheric pressure or under moderate pressures (i.e. 1-10 bar). The flow rates of fusel oils were controlled by Teledyne Model 500D syringe pumps, and the flow rates were adjusted to obtain the targeted olefin WHSV (weight hourly space velocity). The internal reaction temperature was maintained constant via a Lindberg Blue M furnace as manufactured by Thermo-Scientific. Fusel oil conversion and selectivity was calculated by analysis of the liquid phase reactor effluent by GC for organic and water content, and comparing mass accountability fed versus liquid mass collected. Thus, passing a vaporized stream of crude and/or refined Fusel oils over silicated, zirconated, titanated or fluorinated alumina at between 350° C. to 450° C. provides the ability to produce 2-methyl-2-butene in high yields. For comparative purposes, utilizing a commercial grade γ-alumina results in higher levels of 3-methyl-1-butene decreasing the 2-methyl-2-butene single pass yield (see data in Table 1 and 2 below).

Example 1: Impregnated Zr-γ-Alumina (Nominal Metal 6 wt. %) Compared to Commercial Grade γ-alumina Zr-γ-alumina catalyst was prepared by incipient wetness technique. The precursor metal salts (Sigma Aldrich): 2.64 g Zirconium (IV) oxynitrate hydrate was dissolved in deionized water (14.9 ml). Upon salt dissolution, the solution was added in dropwise fashion to 15 g γ-alumina support. The resulting mixed metal oxide was manually mixed to assure complete wetting, and the resulting impregnated catalyst was dried at 160° C. for 1 hr, and afterwards calcined at 500° C. for 4 hrs.

Tables 1 and 2 highlight the difference in selectivity of desirable $C_5$ olefins, via dehydration of crude fusel oils, upon utilization of commercially available γ-alumina versus metal doped γ-alumina at similar reaction conditions. Commercial grade γ-alumina is available from BASF.

TABLE 1

| Reaction Conditions: T = 420° C., WHSV = 2.5; Catalyst - Zirconated (5.6 wt. %) γ-alumina; Fusel Oil Composition: 6.0 wt. % Ethanol, 5.5 wt. % Isobutanol, 54.5 wt. % 3-Methyl-1-butanol, 18.9 wt. % 2-Methyl-1-butanol, 12.1 wt. % Water ||
|---|---|
| Reactor Effluent Composition- | Wt. % of Total: |
| butenes | 3.4 |
| 3-methyl-1-butene | 4.4 |
| 2-methyl-1-butene | 26.8 |
| 2-methyl-2-butene | 60.9 |
| other $C_5$ olefins | 4.1 |
| other $C_2$—$C_3$ olefins | 0.2 |

TABLE 2

| Reaction Conditions: T = 420° C., WHSV = 2.5; Catalyst - Commercial Grade γ-alumina; Fusel Oil Composition: 6.0 wt. % Ethanol, 5.5 wt. % Isobutanol, 54.5 wt. % 3-Methyl-1-butanol, 18.9 wt. % 2-Methyl-1-butanol, 12.1 wt. % Water ||
|---|---|
| Reactor Effluent Composition- | Wt. % of Total: |
| butenes | 5.6 |
| 3-methyl-1-butene | 14.2 |
| 2-methyl-1-butene | 23.1 |
| 2-methyl-2-butene | 46.9 |
| other $C_5$ olefins | 10.1 |
| other $C_2$—$C_3$ olefins | 0.4 |

Prophetic Example 2: Lower Temperature

TABLE 3

Reaction Conditions: T = 375° C., WHSV = 2.5; Catalyst - Zirconated (5.6 wt. %) γ-alumina; Fusel Oil Composition: 6.0 wt. % Ethanol, 5.5 wt. % Isobutanol, 54.5 wt. % 3-Methyl-1-butanol, 18.9 wt. % 2-Methyl-1-butanol, 12.1 wt. % Water

| Reactor Effluent Composition- | Wt. % of Total: |
|---|---|
| butenes | 3.4 |
| 3-methyl-1-butene | 4.0 |
| 2-methyl-1-butene | 26.8 |
| 2-methyl-2-butene | 61.3 |

Prophetic Example 3: Higher Temperature

TABLE 4

Reaction Conditions: T = 525° C., WHSV = 2.5; Catalyst - Zirconated (5.6 wt. %) γ-alumina; Fusel Oil Composition: 6.0 wt. % Ethanol, 5.5 wt. % Isobutanol, 54.5 wt. % 3-Methyl-1-butanol, 18.9 wt. % 2-Methyl-1-butanol, 12.1 wt. % Water

| Reactor Effluent Composition- | Wt % of Total: |
|---|---|
| butenes | 4.2 |
| 3-methyl-1-butene | 2.5 |
| 2-methyl-1-butene | 25.0 |
| 2-methyl-2-butene | 62.8 |

Prophetic Example 4: Fusel Oil Composition

TABLE 5

Reaction Conditions: T = 420° C., WHSV = 2.0; Catalyst - Zirconated (5.6 wt. %) γ-alumina; Fusel Oil Composition: 7.0 wt. % Ethanol, 6.6 wt. % Isobutanol, 54.5 wt. % 3-Methyl-1-butanol, 18.9 wt. % 2-Methyl-1-butanol, 10 wt. % Water

| Reactor Effluent Composition- | Wt % of Total: |
|---|---|
| butenes | 4.2 |
| 3-methyl-1-butene | 2.5 |
| 2-methyl-1-butene | 25.0 |
| 2-methyl-2-butene | 65.0 |

Prophetic Example 5: Zirconated Wt. %

TABLE 6

Reaction Conditions: T = 420° C., WHSV = 2.5; Catalyst - Zirconated (8 wt. %) γ-alumina; Fusel Oil Composition: 10.0 wt. % Ethanol, 5.5 wt. % Isobutanol, 54.5 wt. % 3-Methyl-1-butanol, 16.9 wt. % 2-Methyl-1-butanol, 10.1 wt. % Water

| Reactor Effluent Composition - | Wt. % of Total: |
|---|---|
| butenes | 3.4 |
| 3-methyl-1-butene | 3.4 |
| 2-methyl-1-butene | 27.3 |
| 2-methyl-2-butene | 61.4 |

Prophetic Example 6: Ti Wt. %

TABLE 7

Reaction Conditions: T = 420° C., WHSV = 2.5; Catalyst - Ti (5.6 wt. %) γ-alumina; Fusel Oil Composition: 6.0 wt. % Ethanol, 5.5 wt. % Isobutanol, 54.5 wt. % 3-Methyl-1-butanol, 18.9 wt. % 2-Methyl-1-butanol, 12.1 wt. % Water

| Reactor Effluent Composition - | Wt. % of Total: |
|---|---|
| butenes | 3.6 |
| 3-methyl-1-butene | 3.2 |
| 2-methyl-1-butene | 28.3 |
| 2-methyl-2-butene | 60.4 |

Prophetic Example 7: Si Wt. %

TABLE 8

Reaction Conditions: T = 420° C., WHSV = 2.5; Catalyst - Si (5.6 wt. %) γ-alumina; Fusel Oil Composition: 6.0 wt. % Ethanol, 5.5 wt. % Isobutanol, 54.5 wt. % 3-Methyl-1-butanol, 18.9 wt. % 2-Methyl-1-butanol, 12.1 wt. % Water

| Reactor Effluent Composition- | Wt. % of Total: |
|---|---|
| butenes | 3.0 |
| 3-methyl-1-butene | 5.0 |
| 2-methyl-1-butene | 29.7 |
| 2-methyl-2-butene | 59.4 |

Prophetic Example 8: F Wt. %

TABLE 9

Reaction Conditions: T = 420° C., WHSV = 2.5; Catalyst - F (5.6 wt. %) γ-alumina; Fusel Oil Composition: 6.0 wt. % Ethanol, 5.5 wt. % Isobutanol, 54.5 wt. % 3-Methyl-1-butanol, 18.9 wt. % 2-Methyl-1-butanol, 12.1 wt. % Water

| Reactor Effluent Composition- | Wt. % of Total: |
|---|---|
| butenes | 3.2 |
| 3-methyl-1-butene | 4.0 |
| 2-methyl-1-butene | 26.5 |
| 2-methyl-2-butene | 65.2 |

The following specific examples are intended to be illustrative of the process and catalysts disclosed herein, and should not be construed as limiting the scope of the invention as defined by appended claims.

The foregoing detailed description has been given for clearness of understanding only and no unnecessary limitations should be understood there from as modifications will be obvious to those skilled in the art.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A process for converting fusel oils to renewable chemicals, the process comprising:
contacting a feed stream comprising the fusel oils with an alumina catalyst at a temperature from about 200° C. to about 500° C., and a weight hourly space velocity (WHSV) of at least 1.0, wherein the alumina catalyst comprises one or more of zirconium (Zr), titanium (Ti), silicon (Si), or fluorine (F) in neutral or ionic form; and
forming the renewable chemicals, wherein the renewable chemicals comprise 2-methyl-2-butene in an amount of at least 50 wt. % yield;
wherein the fusel oils comprise ethanol, isobutanol, 3-methyl-1-butanol, and 2-methyl-1-butanol, and wherein the 3 methyl-1-butanol is present in the fusel oils in an amount of about 40 wt. % to about 70 wt. %.

2. The process of claim 1, wherein the fusel oils further comprise propanol, isopropanol, 1-butanol, 2 butanol, tert-butanol, pentanol, 2,2-dimethyl-1-propanol, 3-pentanol, 2-pentanol, 3-methyl-2-butanol, 2-methyl-2-butanol, or any combination thereof.

3. The process of claim 1, wherein the fusel oils further comprise water.

4. The process of claim 1, wherein the fusel oils comprise crude fusel oils, refined fusel oils, or a combination thereof.

5. The process of claim 1, wherein the ethanol is present in the fusel oils in an amount of about 1 wt. % to about 15 wt. %.

6. The process of claim 1, wherein the isobutanol is present in the fusel oils in an amount of about 2 wt. % to about 25 wt. %.

7. The process of claim 1, wherein the fusel oils further comprise a recycled feed stream.

8. The process of claim 1, wherein the renewable chemicals further comprise one or more of 3-methyl-1-butene, 2-methyl-1-butene, $C_2$-$C_5$ olefins, $C_5$ olefins, or $C_2$-$C_3$ olefins.

9. The process of claim 1, wherein the renewable chemicals further comprise 2-methyl-1-butene, which is present in an amount of at least 15 wt. % yield.

10. The process of claim 1, wherein the renewable chemicals further comprise 2-methyl-1-butene, and wherein a ratio of 2-methyl-2-butene to 2-methyl-1-butene by wt. % is from about 2:1 to about 5:1.

11. The process of claim 1, wherein the renewable chemicals further comprise 3-methyl-1-butene, and wherein a ratio of 2-methyl-2-butene to 3-methyl-1-butene by wt. % is from about 10:1 to about 15:1.

12. The process of claim 1, wherein a ratio of 2-methyl-1-butene to 3-methyl-1-butene by wt. % is from about 5:1 to about 10:1.

13. The process of claim 1, wherein the alumina catalyst is a γ-alumina.

14. The process of claim 1, wherein the one or more of Zr, Ti, Si, or F is present in the alumina catalyst in an amount of about 3 wt. % to about 15 wt. %.

15. The process of claim 1 wherein the alumina catalyst is regenerated in-situ via air.

16. The process of claim 15, wherein the alumina catalyst is regenerated at a temperature from about 400° C. to about 600° C.

17. The process of claim 1, wherein contacting the feed stream at a pressure of 0 psig to about 100 psig.

18. A process for converting fusel oils to renewable chemicals, the process comprising:
contacting a feed stream comprising fusel oils with an alumina catalyst at a temperature of about 420° C., and a weight hourly space velocity (WHSV) of about 2.5, wherein the alumina catalyst is γ-alumina and comprises Zirconium (IV); and
forming the renewable chemicals, wherein the renewable chemicals are $C_2$-$C_5$ olefins and further comprises 2-methyl-2-butene in an amount of about 60 wt. % yield;
wherein the fusel oils comprise ethanol, isobutanol, 3-methyl-1-butanol, and 2-methyl-1-butanol, and wherein the 3-methyl-1-butanol is present in the fusel oils in an amount of about 40 wt. % to about 70 wt. %.

* * * * *